(12) United States Patent
Danitz et al.

(10) Patent No.: US 8,273,102 B2
(45) Date of Patent: *Sep. 25, 2012

(54) SURGICAL CLAMP INSERTS WITH HOOKED TRACTION ELEMENTS

(75) Inventors: David J. Danitz, San Jose, CA (US); George D. Hermann, Portola Valley, CA (US); Karrie L. Sturtz, Campbell, CA (US)

(73) Assignee: Vitalitec International, Inc., Plymouth, MA (US)

( * ) Notice: Subject to any disclaimer, the term of this patent is extended or adjusted under 35 U.S.C. 154(b) by 1655 days.

This patent is subject to a terminal disclaimer.

(21) Appl. No.: 10/861,757

(22) Filed: Jun. 4, 2004

(65) Prior Publication Data

US 2005/0059988 A1  Mar. 17, 2005

Related U.S. Application Data

(63) Continuation-in-part of application No. 10/664,273, filed on Sep. 16, 2003.

(51) Int. Cl.
A61B 17/00 (2006.01)
(52) U.S. Cl. .................................................. 606/207
(58) Field of Classification Search .......... 606/207, 606/205, 151
See application file for complete search history.

(56) References Cited

U.S. PATENT DOCUMENTS

| | | | |
|---|---|---|---|
| 2,706,987 A | 4/1955 | Bramstedt | |
| 2,717,437 A | 9/1955 | De Mestral | |
| 3,009,235 A | 11/1961 | De Mestral | |
| 3,192,589 A | 7/1965 | Pearson | |
| 3,408,705 A | 11/1968 | Kayser et al. | |
| 3,509,882 A | 5/1970 | Blake | |
| 3,594,863 A | 7/1971 | Erb | |
| 3,594,865 A | 7/1971 | Erb | |
| 4,290,174 A | 9/1981 | Kalleberg | |
| 4,794,028 A | 12/1988 | Fischer | |
| 4,821,719 A * | 4/1989 | Fogarty | 606/158 |
| 4,846,815 A | 7/1989 | Scripps | |
| 4,931,058 A | 6/1990 | Cooper | |
| 4,963,140 A | 10/1990 | Robertson et al. | |
| 4,984,339 A | 1/1991 | Provost et al. | |
| 5,019,065 A | 5/1991 | Scripps | |
| 5,077,870 A | 1/1992 | Melbye et al. | |
| 5,260,015 A | 11/1993 | Kennedy et al. | |
| 5,315,740 A | 5/1994 | Provost | |
| 5,318,555 A | 6/1994 | Siebers et al. | |
| 5,339,499 A | 8/1994 | Kennedy et al. | |
| 5,518,795 A | 5/1996 | Kennedy et al. | |

(Continued)

FOREIGN PATENT DOCUMENTS

JP  63068153  3/1988

(Continued)

OTHER PUBLICATIONS

U.S. Appl. No. 10/349,871, filed Jan. 22, 2003, Sturtz et al.

(Continued)

*Primary Examiner* — Katherine Dowe
(74) *Attorney, Agent, or Firm* — Bachman & LaPointe, P.C.

(57) ABSTRACT

Compliant inserts for surgical instruments having improved traction are provided. The clamping surface of the inserts includes a plurality of short and densely arranged traction elements. The tractive force supplied by the traction elements approaches that of steel jawed clamps.

27 Claims, 14 Drawing Sheets

U.S. PATENT DOCUMENTS

| | | | |
|---|---|---|---|
| 5,607,635 | A | 3/1997 | Melbye et al. |
| 5,653,720 | A | 8/1997 | Johnson et al. |
| 5,664,301 | A | 9/1997 | Akeno |
| 5,679,302 | A | 10/1997 | Miller et al. |
| 5,728,121 | A | 3/1998 | Bimbo et al. |
| 5,845,375 | A * | 12/1998 | Miller et al. .................... 24/452 |
| 5,865,730 | A | 2/1999 | Fox et al. |
| 5,893,878 | A | 4/1999 | Pierce |
| 6,007,552 | A | 12/1999 | Fogarty et al. |
| 6,099,539 | A | 8/2000 | Howell et al. |
| 6,165,186 | A | 12/2000 | Fogarty et al. |
| 6,187,247 | B1 | 2/2001 | Buzzell et al. |
| 6,206,896 | B1 | 3/2001 | Howell et al. |
| 6,228,104 | B1 | 5/2001 | Fogarty et al. |
| 6,267,773 | B1 | 7/2001 | Gadberry et al. |
| 6,273,902 | B1 | 8/2001 | Fogarty et al. |
| 6,387,106 | B1 | 5/2002 | Howell et al. |
| 6,387,112 | B1 | 5/2002 | Fogarty et al. |
| 6,484,371 | B1 * | 11/2002 | Romanko et al. ............... 24/306 |
| 6,526,633 | B2 | 3/2003 | Provost et al. |
| 6,558,602 | B1 | 5/2003 | Melbye et al. |
| 2002/0072766 | A1 * | 6/2002 | Hunt et al. .................... 606/205 |

FOREIGN PATENT DOCUMENTS

| | | |
|---|---|---|
| JP | 6500486 | 1/1994 |
| JP | 8506754 | 7/1996 |
| JP | 11226021 | 8/1999 |
| JP | 2002508205 | 3/2002 |
| WO | WO 98/33437 | 8/1998 |
| WO | WO 99/11179 | 3/1999 |
| WO | 9930623 | 6/1999 |

OTHER PUBLICATIONS

Japanese Office Action on Application No. 2006-526424 dated Oct. 19, 2010.

Japanese Office action for Patent Application No. 2006-526424 dated Jan. 14, 2010.

Translation of Japanese Office action for Patent Application No. 2006-526424, Feb. 8, 2010.

* cited by examiner

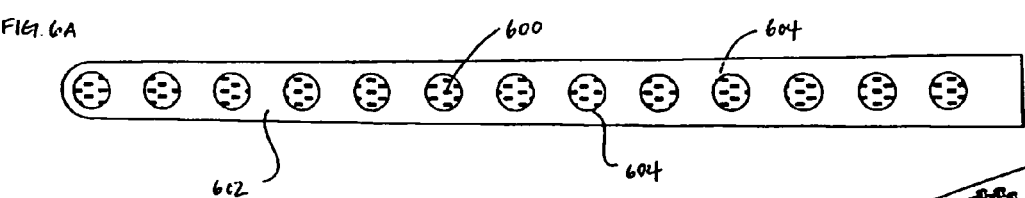
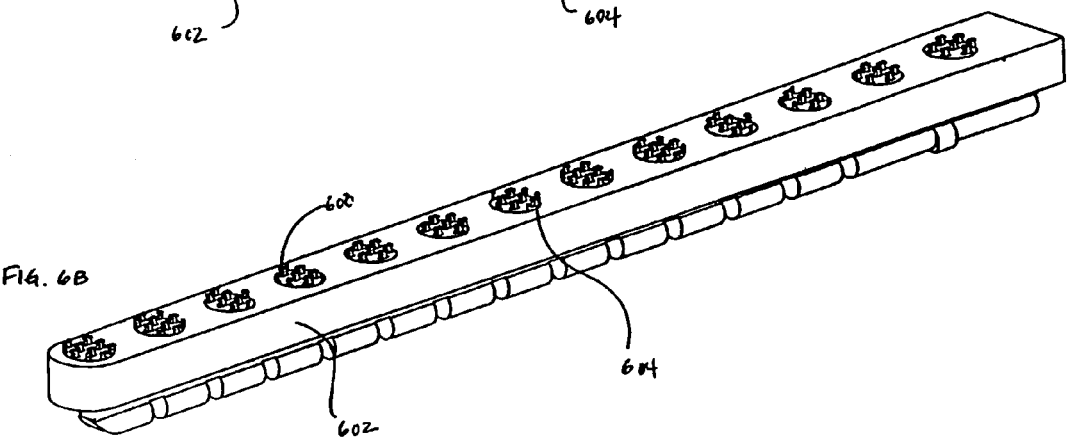

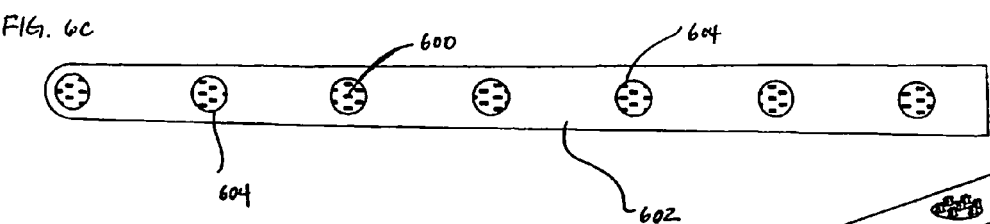
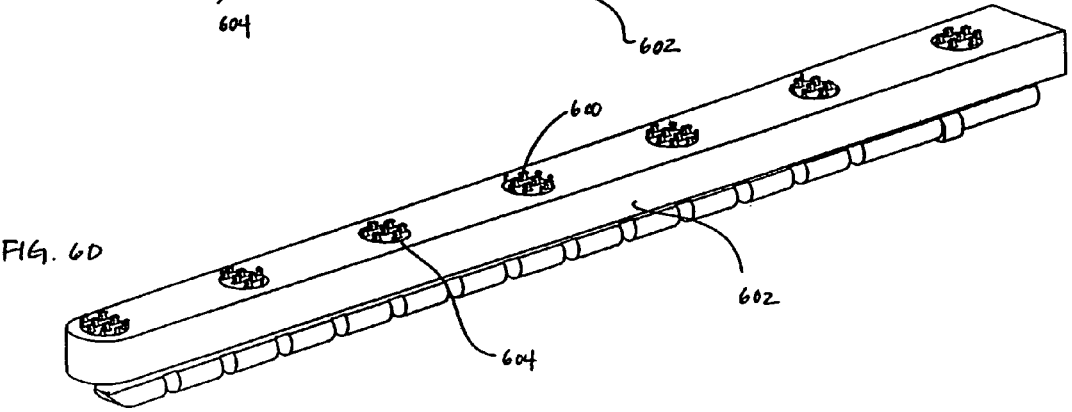

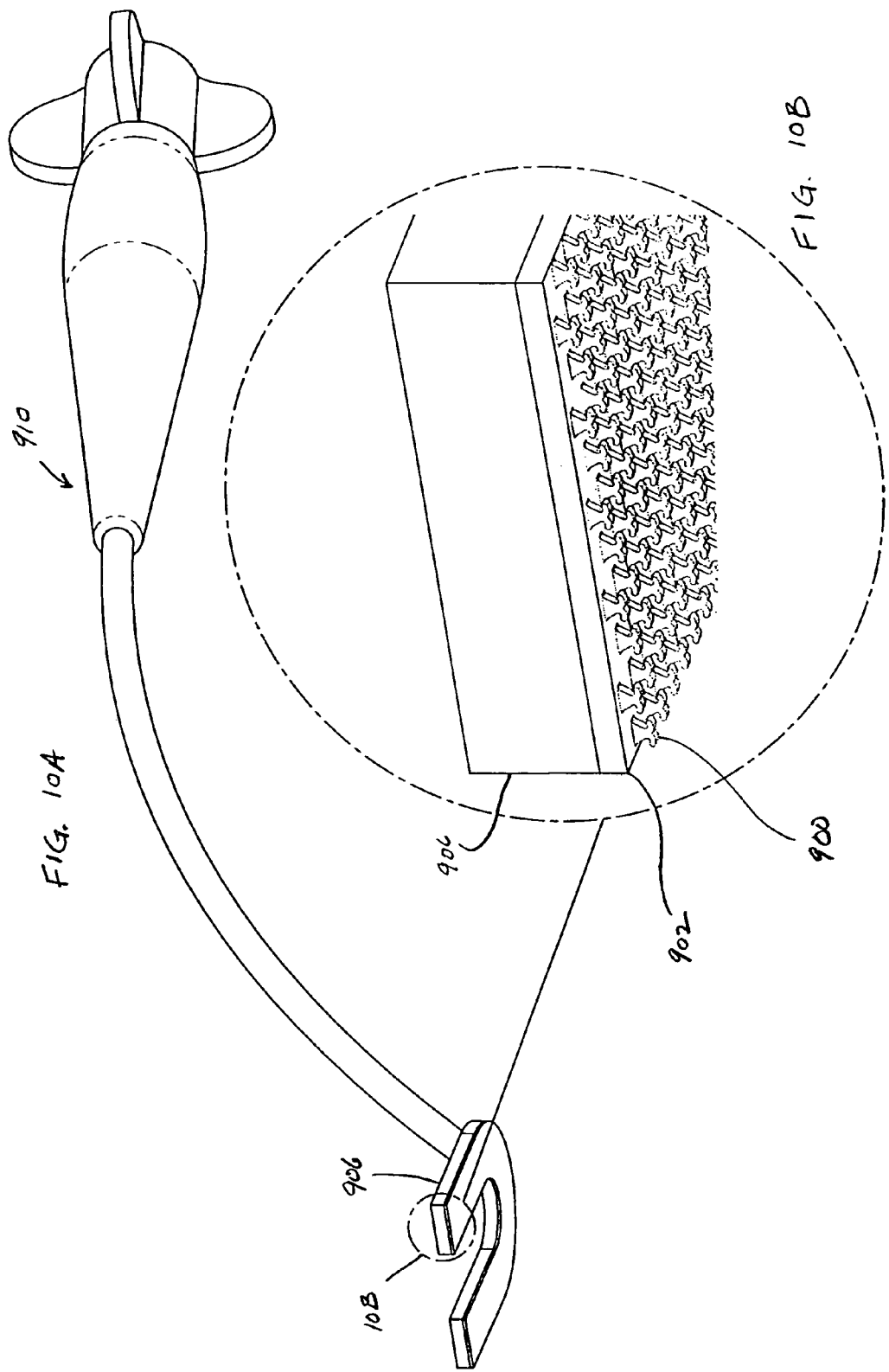

SURGICAL CLAMP INSERTS WITH HOOKED TRACTION ELEMENTS

CROSS-REFERENCE TO RELATED APPLICATIONS

This application is a continuation-in-part of U.S. Ser. No. 10/664,273, filed Sep. 16, 2003, the contents of which is hereby incorporated by reference into the present disclosure.

FIELD OF THE INVENTION

This invention relates to atraumatic, surgical instruments, including but not limited to surgical clamps and clips. Specifically, the instruments include engaging surfaces that provide increased traction on body tissues.

BACKGROUND OF THE INVENTION

Surgical instruments having hard jaw surfaces (e.g., made of steel or other hard plastic or composite materials) have been employed in many surgical procedures for retracting, and/or immobilizing tissues or organs, positioning grafts or catheters, and occluding tubular structures, e.g., blood vessels and ducts and other body conduits. Instruments for occluding blood vessels and other body conduits, including jaw-type occlusion instruments, are well-known. In particular, surgical clamps commonly used for occlusion typically include pivoting jaw members that are moveable toward one another and which are actuated by handle members extending from the jaw members. The handle members typically include a ratchet mechanism to hold the engaged clamp in place. Surgical clips are commonly used to occlude smaller blood vessels and other body conduits during surgical procedures. A common type of surgical clip is the parallel jaw clip that includes a pair of jaws oriented generally parallel to one another and moveable from an open to a closed position. Many such clips include compression or extension springs for biasing the jaws together in the closed position. Representative of such clips are those described in, e.g., U.S. Pat. Nos. 3,509,882, 4,931,058, 5,653,720 and 6,267,773. Such clips have gained wide acceptance and are easy to place and remove, and provide for dependable occlusion, and are also useful for other applications, such as suture tags and identification markers.

Many conventional surgical clamps and clips are made of metal, such as stainless steel, hard plastic, or other similarly rigid materials. Such surgical clamps and clips are favored for a number of reasons. They can be manufactured to have a low profile, and the overall structural rigidity of the clamps or clips together with non-deflectable and non-deformable gripping surfaces provides for clamps and clips having good gripping properties. A disadvantage of such clamps and clips is that the hard surfaces and rigidity of the clamps can cause trauma to the clamped vessel at the site of occlusion. Further, in order to improve instrument hold on tissues, such jaws are often manufactured to be variously grooved or serrated. While obtaining superior gripping capabilities, these types of jaw surfaces have been associated with a certain degree of trauma to the gripped tissue.

As a result, a number of atraumatic versions of surgical clamps and clips have been developed for reducing trauma to a vessel during occlusion. In particular, such clamps and clips have been adapted to include jaw surfaces containing cushioned pads, members or inserts. These pads, members or inserts are usually made from easily deformable materials. Due to the increased compliance of these pads, members or inserts, the tractive force applied is often compromised, resulting in undesirable slippage, and in some cases the inserts are prone to slipping off the clamped vessel, especially where the clamps or clips are engaged near the distal ends of their jaws. Also, due to the deformability of such pads, members or inserts, they likewise can be prone to slipping laterally along a clamped vessel, which can further result in a scissoring effect where the jaws twist off-line. In all such situations, effective clamping is compromised.

Methods to improve the tractive force imparted by atraumatic inserts have been attempted, typically by modifying the clamping surfaces of the inserts. For example, FIBRA™ clamp inserts (Applied Medical, Rancho Santa Margarita, Calif.) are covered with a woven layer of flexible, soft, finger-like nylon fibers to help grip vessel adventitia. Similar inserts are disclosed in U.S. Pat. No. 4,821,719 to Fogarty.

U.S. Pat. Nos. 6,099,539; 6,206,896; and 6,387,106 to Howell et al. describe another type of atraumatic insert. These inserts are described as having uniform raised protrusions which interdigitate when the clamp jaws are moved toward one another.

PCT application WO 98/33437 discloses an atraumatic clamping surface with bristles to improve traction. The bristles may be made from polyethylene or nylon and can be provided on the insert in an upright or slanted orientation. When the bristles contact tissue, e.g., a vessel, they crumple in the area immediately adjacent to the vessel. Traction is then provided by the bristles on the sides of the vessel, which block its lateral movement.

PCT Publication WO 99/11179 discloses inserts consisting of a compliant cushion covered with a mesh surface overlay.

U.S. application Ser. No. 10/349,871, filed Jan. 22, 2003, discloses inserts having integrally formed raised patterns that extend from the cushion surface.

Despite the numerous attempts to improve the tractive properties of atraumatic inserts, there remains a need for jaw-type surgical instruments with atraumatic inserts having improved grasping capabilities, including atraumatic inserts that can approach or match the gripping and traction supplied by conventional steel jawed instruments.

Similarly, conventional tissue retractors and graspers are well known which retract, grasp or otherwise manipulate tissue at a surgical incision site to e.g. provide a surgeon visual and mechanical access to the interior of a patient's body. These tissue retractors and graspers typically employ rigid gripping members, again usually of metal, hard plastic or other rigid material, to grip, retract, and retain and/or grasp all forms of body tissue, e.g., bone, skin, fat, or muscle, or body organs, e.g., liver, intestine, etc., at the incision site. Such rigid gripping members can cause trauma to the retained or grasped tissues.

Other surgical instruments or devices are known that provide for mechanical immobilization and stabilization of tissue or organs within a surgical incision site. These instruments or devices, typically known as stabilizers, will immobilize, stabilize, or otherwise restrain tissue or organs by exerting pressure against a tissue or organ to hold the tissue or organ in place, aiding a surgeon performing operations on the tissue or organ. Such stabilizers have particular use, for example, in minimally invasive coronary surgery procedures. For example, coronary artery stabilizers have been used to immobilize a beating heart in order to perform coronary grafting. These stabilizers achieve immobilization largely by local myocardial compression from direct pressure applied by the stabilizer on either side of the grafted artery. These stabilizers come in a variety of shapes, including e.g., open foot-shaped devices, and rigid circle or rectangular shapes, and may be either hand held, or attached to an incisional retractor located at the incision site. Another such example of a stabilizer device consists of a system having two fixed handles having suction cups that are positioned on either side of the vessel.

Given the amount of pressure transferred to the myocardium during the use of these stabilizers, there is a danger that the contact surfaces of these stabilizer devices will traumatize the myocardial tissue. In addition, the forces exerted by the immobilized but still beating heart can lead to a shift in alignment of the stabilizer, which can disrupt the grafting procedure.

Thus, there also remains a need for retractors, graspers, stabilizers and the like with tissue-engaging surfaces that atraumatically retract, grasp, manipulate and/or immobilize a tissue or body organ, and yet at the same time provide improved traction.

BRIEF SUMMARY OF THE INVENTION

The present invention meets these and other needs and provides for inserts that may be permanently mounted or releasably attached to tissue-engaging surfaces of surgical instruments such as clamps, clips, and forceps, as well as to tissue retractors, stabilizers, and other like surgical instruments used to grasp, retain, immobilize, contact or otherwise engage tissues or organs.

The invention is based on the discovery that inserts of compliant cushions having a tissue-engaging contact surface and a plurality of hooked traction elements provided on at least a region of the contact surface provide improved traction while minimizing trauma to contacted tissue, including grasped or occluded tissue. In variations of the invention, the hooked, traction elements can be molded. Molded, hooked traction elements may be integrally formed with the contact surface, or alternatively can be integrally molded onto strips or sheets of material which can then be adhered in various configurations to the contact surface. The hooked, traction elements can be provided on the entire contact surface area of the insert, or alternatively can be provided on a discrete region or regions of the contact surface area.

As used herein, the term "hooked traction elements" refers to traction elements that have at least a stem and a head or lateral extension extending therefrom of any shape known in the art, including but not limited to, e.g., single crook, twin crook (two crooks), flat-topped hook, or mushroom-like hook shapes. The pattern of traction elements on a discrete region or regions of the insert contact surface may be, but is not limited to, generally uniform, repeated patterns of traction elements.

The hooked traction elements of the present invention are generally shorter than, for example, the traditional woven "J" shaped hooks found on fasteners described, e.g., in U.S. Pat. Nos. 2,717,437 and 3,009,235 to DeMestral, and marketed under the trademark VELCRO by Velcro USA, Inc. In general, the hooked traction elements will not be more than about 1 mm (about 0.04 inches) in height. In certain instances, they will be not more than about 0.5 mm (about 0.02 inches) in height, or not more than about 0.3 mm (about 0.01 inches) in height.

The density of the hooked traction elements per unit area of the surface region or regions of the insert containing the traction elements is, in general, relatively high. Such densities may vary further with such factors as the size, shape, and method of manufacture of the traction elements. For example, the density of traction elements per unit area of the surface region or regions of the insert containing the traction elements may be at least about 100 traction elements/cm$^2$. In certain instances, the density may be at least about 130 traction elements/cm$_2$, or least about 260 traction elements/cm$^2$, or at least about 300 traction elements/cm$^2$.

The inserts are typically attached to the jaws of surgical clamps and clips or to the tissue contacting regions of other instruments, such as stabilizers or retractors. When such inserts are adapted for and placed on the jaws of typical surgical clamps, a tractive force between about 4 to about 10 pounds is provided on a vessel clamped by the clamp. When such inserts are adapted for and placed onto typical parallel-jaw spring clips, a tractive force between about 1.5 to about 2.5 pounds is provided on a vessel clamped by the clip. The inventive inserts, whether attached to clamp or clip jaws, provide more traction on clamped vessels than currently marketed atraumatic versions, and provide traction levels that approach those found with conventional steel jawed clamps and clips.

The invention and its advantages will be even more apparent in view of the following description and accompanying drawings.

BRIEF DESCRIPTION OF THE DRAWINGS

FIG. 1A is a side view; FIG. 1B is a perspective view; and FIG. 1C is a top view which also shows the arrangement of traction elements with respect to one another.

FIG. 2A is a side view; FIG. 2B is a perspective view; and FIG. 2C is a top view which also shows the arrangement of traction elements with respect to one another.

FIG. 3A is a side view; FIG. 3B is a perspective view; FIG. 3C is a top view which also shows the arrangement of traction elements with respect to one another.

FIGS. 6A-6D, 7A-7B and 8A-8B show inserts according to multiple variations of the invention with regions of molded, hooked traction elements in arranged different patterns on the tissue-contacting surfaces of the inserts. In the variation depicted in FIGS. 6A-6B, the traction elements of FIGS. 1A-1C are arranged in a repeating pattern of closely spaced circles. FIG. 6A is a top view of the insert and FIG. 6B is a perspective view of the insert. In FIGS. 6C-6D, the traction elements of FIGS. 1A-1C are arranged in a pattern of more widely spaced circles. FIG. 6C is a top view of the insert and FIG. 6D is a perspective view of the insert. In FIGS. 7A-7B, the traction elements of FIGS. 1A-1C are arranged in a repeating pattern of ovals. FIG. 7A is a top view of the insert and FIG. 7B is a perspective view of the insert. In FIGS. 8A-8B, the traction elements of FIGS. 1A-1C are arranged in a repeating pattern of diamonds. FIG. 8A is a top view of the insert and FIG. 8B is a perspective view of the insert.

FIG. 10A is a perspective view of a surgical stabilizer having a tissue contacting surface; FIG. 10B is an enlarged view of a portion of the tissue contacting surface, showing the surface having the molded, hooked traction elements of FIGS. 1A-1C.

DETAILED DESCRIPTION OF THE INVENTION

Figure 1A:
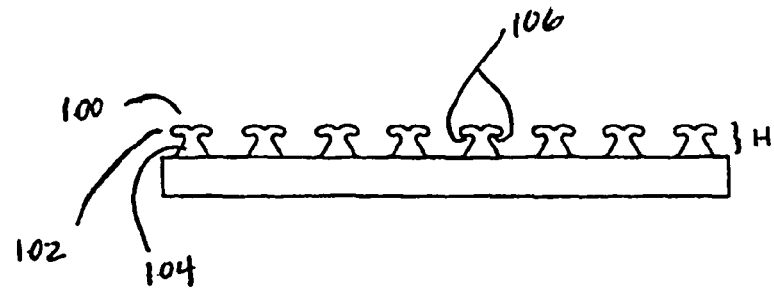
FIGS. 1A-1C show molded hooked traction elements according to one variation of the invention having a repeating pattern of twin crooks.

The inserts of this invention may be mounted onto various surgical instruments to minimize trauma to tissues or organs that are manipulated, e.g., grasped, clamped, retracted, retained or immobilized by the instrument. Examples of surgical instruments include, but are not limited to, clamps, clips, forceps, graspers, retractors and stabilizers, as well as other instruments generally designed to grasp, retain, immobilize, contact or otherwise engage tissue or bodily organs. Instruments equipped with these inserts provide atraumatic traction on tissues or organs without having to increase the clamping or resistive force on the tissue or organ.

Hooked traction elements employed on inserts according to the invention differ in many ways from traditional woven, cut loop hook fasteners sold, for example, under the brand names VELCRO™ (Part Nos. Hook #65 and Hook #88, Velcro USA, Inc., Manchester, N.H.) and SCOTCHMATE™ (Part No. SJ-3401, Minnesota Mining and Manufacturing Co., St. Paul, Minn.). For example, in certain variations of the invention, the hooked traction elements are molded, rather than woven. The traction elements may be fabricated by known techniques, such as injection molding and compression molding, and as specifically described in U.S. Pat. Nos. 3,594,865 and 3,594,863 to Erb; U.S. Pat. No. 4,794,028 to Fischer; U.S. Pat. No. 5,260,015 and 5,518,795 to Kennedy et al.; and U.S. Pat. No. 6,187,247 to Buzzell et al. Also, the hooked traction elements of the invention and are also relatively smaller in height and can be arrayed at much higher densities on surface regions of the inserts, as compared to conventional woven, cut loop hook fasteners.

The hooked traction elements are formed to have at least one stem extending from the insert tissue contacting surface, and at least one head or lateral extension extending from the stem. As described above, the hooked traction elements are typically configured as hooks, with the term "hooks" encompassing a variety of shapes known in the art, including but not limited to, e.g., hooks with a single crook, twin crooks, a flat top, a mushroom-type shape, and the like. Suitable hook shapes are described in U.S. Pat. No. 3,192,589 to Pearson; U.S. Pat. No. 3,408,705 to Kayser et al.; U.S. Pat. No. 4,290,174 to Kalleberg; U.S. Pat. Nos. 4,984,339 and 6,526,633 to Provost et al.; U.S. Pat. No. 5,315,740 to Provost; U.S. Pat. No. 5,339,499 to Kennedy et al.; U.S. Pat. No. 5,664,301 to Akeno; U.S. Pat. No. 5,679,302 to Miller et al; and U.S. Pat. No. 5,845,375 to Miller et al. Commercially available fastening materials can provide a source of traction elements. Fastener materials found on disposable absorbent articles such as described in U.S. Pat. Nos. 4,846,815 and 5,019,065 to Scripps; U.S. Pat. No. 4,963,140 to Robertson et al.; and U.S. Pat. No. 5,318,555 to Siebers et al. may also provide sources of traction elements.

Traction element dimensions may vary, but usually the height of each traction element will be chosen to be about 1 mm (about 0.04 inches) or less. In certain variations, the height can be about 0.8 mm (about 0.03 inches) or less, or about 0.5 mm (about 0.02 inches) or less, or about 0.4 mm (about 0.015 inches) or less, or about 0.3 mm (about 0.01 inches) or less. As a comparison, FIBRA™ clamp inserts (Applied Medical, Rancho Santa Margarita, Calif.) are covered with a woven layer of flexible, soft, finger-like nylon fibers that closely resembles traditional woven, cut loop hook fasteners; the hook shaped fibers are approximately 1.5 mm (about 0.060 inches).

The density of the traction elements per unit area of the contact surface region or regions on the insert containing the traction elements will also vary with such factors as the overall configuration of the element, the particular shape, orientation, and width or diameter of element stems or heads, and the distance between elements. In general, traction element dimensions and densities will also vary by the manufacturing parameters and processes employed. However, a density of at least about 100 elements per square centimeter is desirable. In certain variations, densities of at least about 130 elements, or at least about 160 elements, or at least about 200 elements, or at least about 230 elements, or at least about 260 elements, or at least about 300 elements per square centimeter is desirable. Again as a comparison, FIBRA™ clamp inserts (Applied Medical, Rancho Santa Margarita, Calif.) are covered with a woven layer of flexible, soft, finger-like nylon fibers that closely resembles traditional woven, cut loop hook fasteners, and that are arranged at a density of about 62 hook shaped fibers per square centimeter.

Figure 1B:
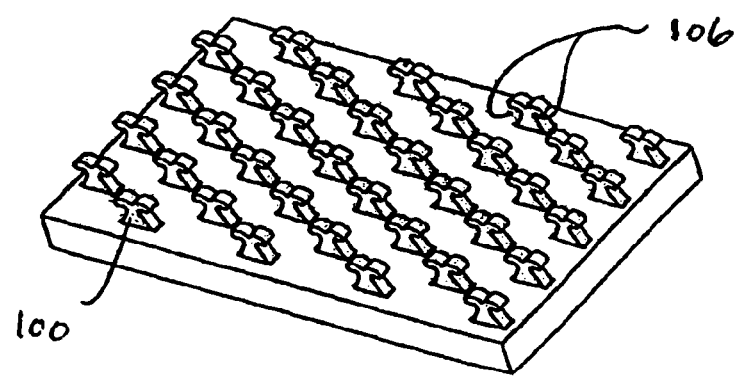
Figure 1C:
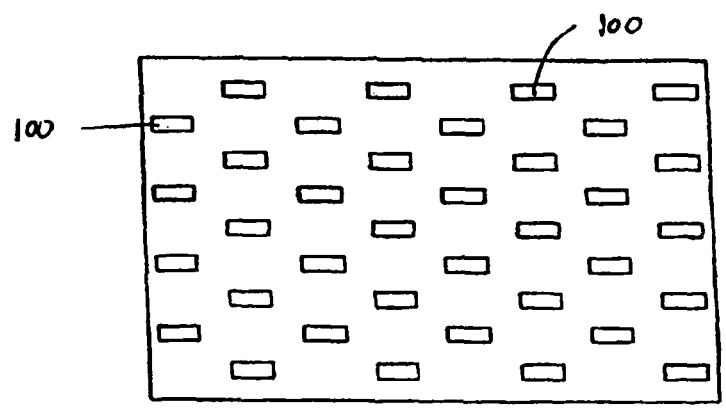

FIGS. 1A-1C show traction elements according to one aspect of the present invention. In FIG. 1A, traction element 100 has a head 102 and stem 104. The height (H) of each traction element 100 is about 0.4 mm. As shown more clearly in FIG. 11B, the traction elements 100 are configured to have twin crooks 106. FIG. 1C shows that the traction elements 100 are arranged such that each row is vertically and horizontally offset from one another. The traction elements are arranged at a density of about 130 elements/cm$_2$.

Figure 2A:
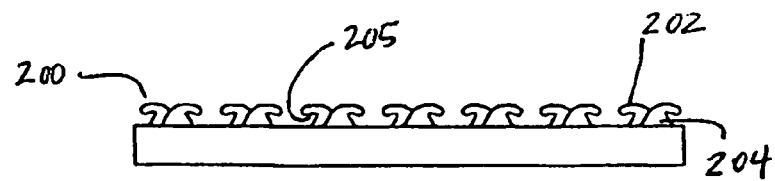
FIGS. 2A-2C show molded hooked traction elements according to another variation of the invention having a repeating pattern of single crooks.
Figure 2B:
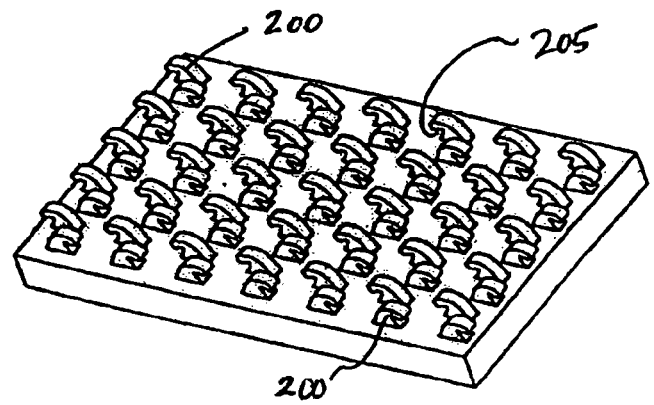
Figure 2C:
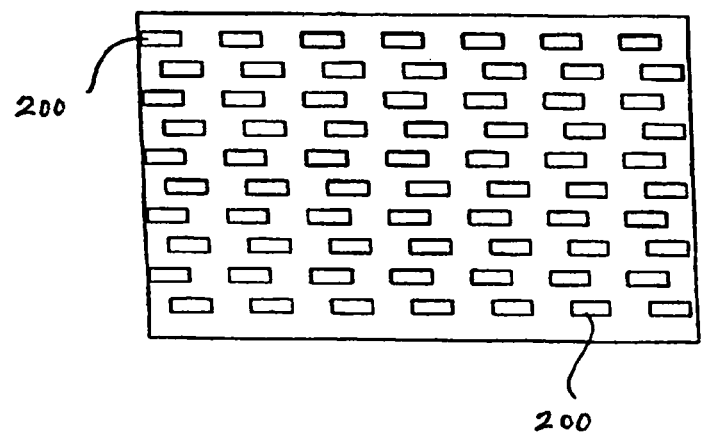

FIGS. 2A-2B show traction elements according to another aspect of the invention. As shown in FIG. 2A, the traction elements 200 also have a head 202 and stem 204 portion. However, instead of a twin crook, the traction elements 200 are configured to have a single crook 205. In FIGS. 2B and 2C, the horizontal rows of traction elements 200 are shown to be spaced closer than those in FIGS. 1B and 1C. The traction elements are arranged at a density of about 260 elements/cm$^2$.

Figure 3A:
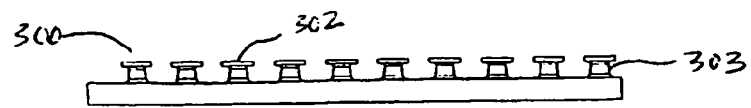
FIGS. 3A-3C show molded hooked traction elements according to yet another variation of the invention having a repeating pattern of hooks with a mushroom-type head.
Figure 3B:
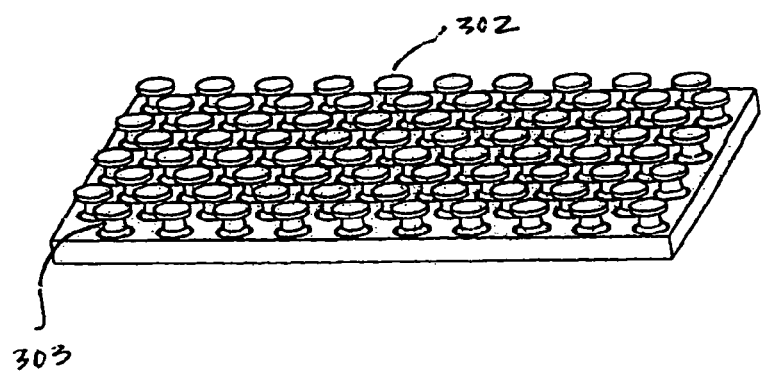
Figure 3C:
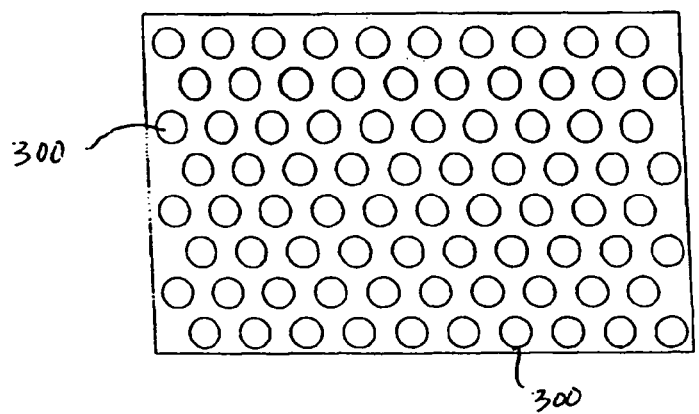

FIGS. 3A-3C show traction elements according to yet another aspect of the invention. In this aspect, the traction elements 300 have a disc-shaped head 302 that is generally flat, but which may also be slightly concave, and a stem 303. The shape of the heads 302 is more clearly depicted in FIG. 3B. The height of the traction elements 300 is about 0.3 mm (about 0.01 inches). The diameter of the heads 302 is about 0.4 mm (about 0.015 inches). In FIGS. 3B and 3C, the horizontal rows of traction elements 300 are shown to be uniformly spaced apart. The traction elements are arranged at density of about 300 elements/cm$^2$.

The traction elements may be made from a variety of thermoplastic or thermosetting polymers such as polyethylene, polypropylene, nylons, melamine, polystyrenes, polycarbonates, various fluorinated polymers, epoxy resin, cellulose acetate, vinyl chloride polymers, and copolymers or blends thereof, such as described in U.S. Pat. No. 3,408,705 to Kayser et al.; U.S. Pat. No. 3,594,865 to Erb; U.S. Pat. No. 4,963,140 to Robertson et al.; and U.S. Pat. No. 6,526,633 to Provost et al.

Inserts according to the invention can be formed of a variety of compliant materials known in the art to minimize tissue trauma. For example, elastomeric materials that are compliant and resiliently deflectable are suitable. Such elastomeric materials include, but are not limited to, natural rubber, neoprene, urethane, ethyl vinyl acetate foam, silicone, or silicone foam. It is desirable that the material be a thermoplastic elastomer suitable for injection molding such as styrenic based thermoplastic elastomers or other thermoplastic elastomers and, in particular, those available in the 0-95 Shore A range. The inserts may be attached or affixed to surgical instruments by mechanical bonding, adhesives, direct injection molding onto the instruments, or by other known means.

In the case of surgical clamps, such inserts can be bonded or adhered to, or otherwise overmolded onto known attachment structures, including rigid attachment structures, for securement onto surgical clamps. (See e.g. FIBRA™ Surgical Clamp Inserts, Applied Medical, Rancho Santa Margarita, Calif., Model No. G-8655; ENGAGE™ Inserts, Novare Surgical, Cupertino, Calif., Model No. N-10103). Alternatively, the insert can be secured to a surgical instrument, e.g., a clamp jaw, by means described in U.S. Pat. Nos. 6,228,104, 6,273,902, and 6,387,112, each commonly owned by the assignee of the present application and incorporated herein in its entirety. Briefly, such means include a flexible elongate attachment member configured to be received in an elongate cavity or channel that extends longitudinally of a clamped jaw. Such attachment members can be formed of a plastic that is flexible but generally stiffer and markedly less deflectable than the insert material. Suitable materials include nylon or polypropylene. Such a design is especially advantageous in that the resulting insert can accommodate a variety of jaw shapes and configurations, including curved jaws. Inserts according to the present invention and having such attachment members are depicted in FIGS. 4-8. In the case of surgical clips, such inserts can be overmolded directly onto the clip jaw or can otherwise be attached or bonded to the clip jaw through known methods.

In some instances, it may be desirable to form the insert overmold from a single elastomer. However, more than one overmold may be made. As depicted in FIGS. 9A-9D, a second overmold 508 made from an elastomer having a shore durometer rating of about 2 A to about 95 A is molded over a more rigid, but still flexible first overmold 510 made from an elastomer having a shore durometer rating of about 20 A to about 95 A. The inserts may also be formed to have a level surface or one or more wells. Furthermore, the inserts may be injection molded directly onto surgical instruments, or may otherwise be affixed to them by mechanical bonding, adhesives, or other known means. For example, FIGS. 10A and 10B depict stabilizer 910 with insert 902 affixed to stabilizing arm 906 of the stabilizer. As shown, insert 902 includes traction elements 900 similar to those depicted in FIGS. 1A-1C.

The traction elements may be integrally molded with the insert or if provided on sheets or strips of a polymer material, placed onto the inserts by methods including, but not limited to, e.g., ultrasonic welding, heat bonding, or bonding with a number of available adhesives such as urethanes, epoxies, cyanoacrylates and pressure-sensitive adhesives. When supplied on sheets or strips, the traction elements will usually be cut out into various strips or patterns and then placed on the inserts. If the insert has been provided with a recessed region or regions, the cut out patterns may be laid in such region(s). In addition, the traction elements may be patterned on the inserts in repeating or non-repeating shapes, such as rectangles, circles, ovals, diamonds, and the like. Connecting arms or spines of narrower width may or may not be included to connect the individual shapes. The shapes may also be placed upon the inserts such that they are touching one another or spaced apart from one another.

Figure 4A:
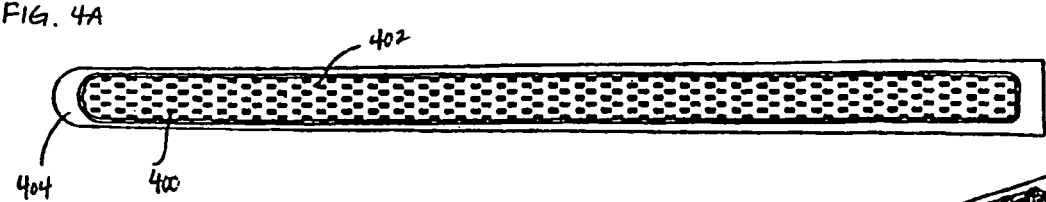
FIG. 4A is a top view of an insert according to one variation of the invention having traction elements according to FIGS. 1A-1C secured as a continuous strip of uniform width to the tissue-contacting surface on the insert.

For example, in one aspect, as illustrated in FIG. 4A, continuous strip 402 of uniform width with traction elements 400 has been cut out and placed on insert 404. As further depicted in FIG. 4B, strip 402 may lie in recessed region 406 formed in insert 404.

Figure 5A:
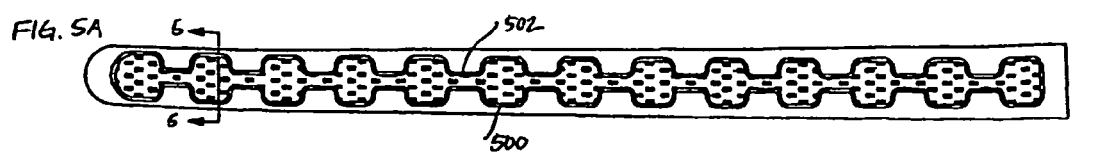
FIG. 5A is a top view of an insert according to another variation of the invention having traction elements according to FIGS. 1A-1C secured as a continuous strip of alternating wider and narrower widths to the tissue-contacting surface of the insert.
Figure 5B:
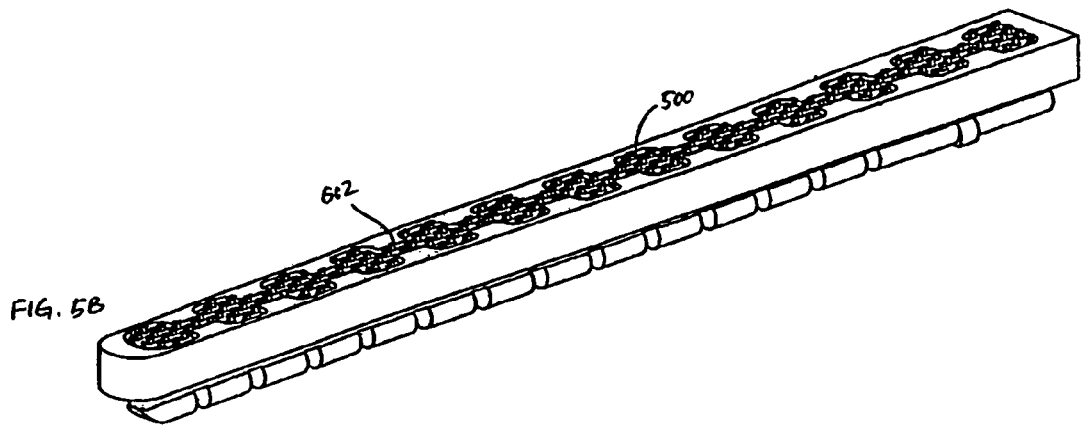
FIG. 5B is a perspective view of the insert shown in FIG. 5A.

FIGS. 5A and 5B show another variation of the traction element pattern. In this variation, the sheet or strip of traction elements has been cut to form rectangles 500. The rectangles 500 are connected to each other by spines 502 of narrower width. These spines of narrower width improve the lateral flexibility of the insert. Rectangles 500 and spines 502 are cut as a unit from the sheet or strip of traction elements, i.e., they are not separate pieces applied to the insert.

FIGS. 6A-6D show traction elements 600 placed in a circular pattern on insert 602. The diameter of each circle 604 is about 2 to about 2.5 mm. In FIGS. 6A-6B, circles 604 are spaced about 3 to about 4 mm apart. In FIGS. 6C-6D, circles 604 are spaced about 6 to about 10 mm apart.

Figure 7A:
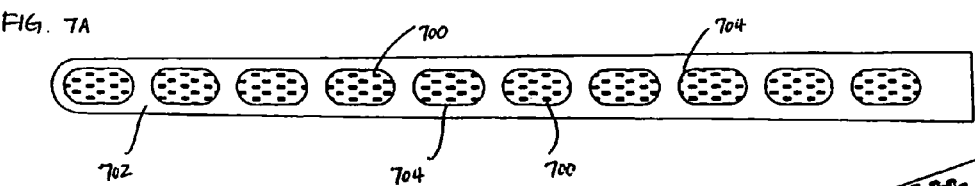
Figure 7B:
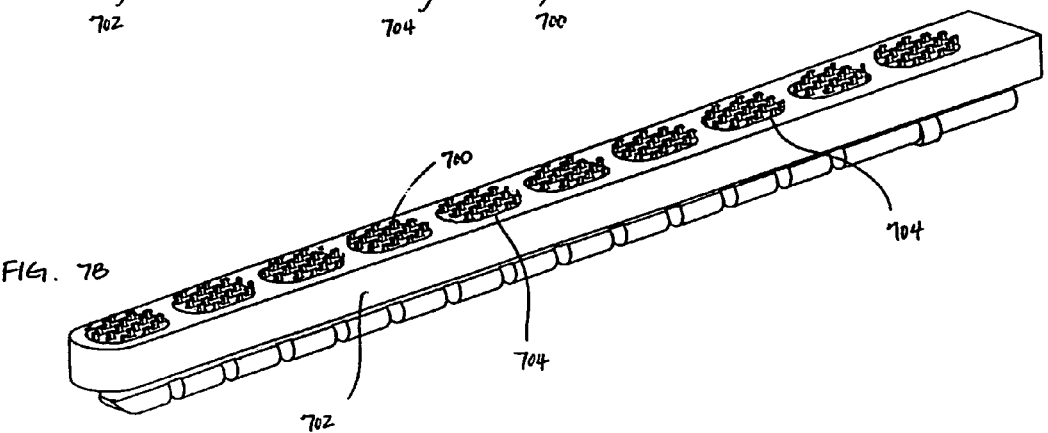

FIGS. 7A-7B show traction elements 700 placed in repeating oval patterns on insert 702. Ovals 704 are about 5 mm long and about 2.5 mm wide. Each oval 704 is spaced about 2 to about 3 mm apart.

Figure 8A:
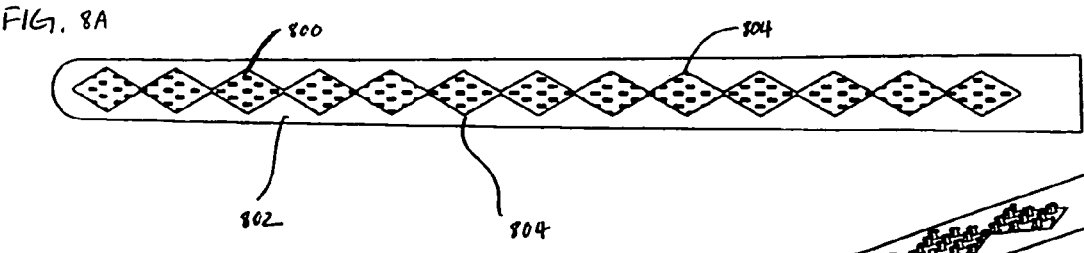
Figure 8B:
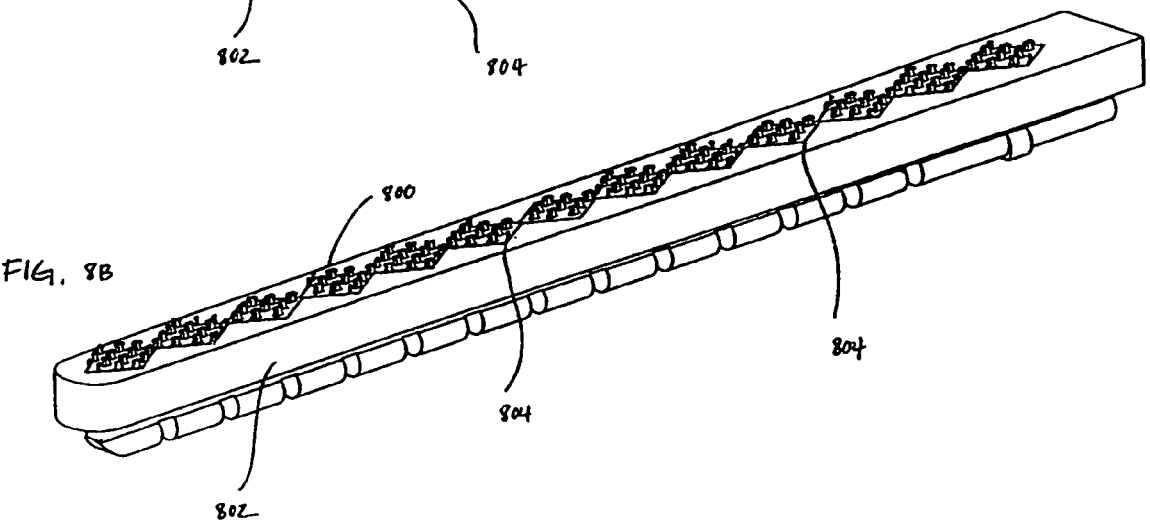

FIGS. 8A-8B show traction elements 800 placed in a touching diamond pattern on the insert 802. Diamonds 804 are about 2.5 to about 3 mm in length and about 2.5 to about 3 mm in width.

Figure 9A:
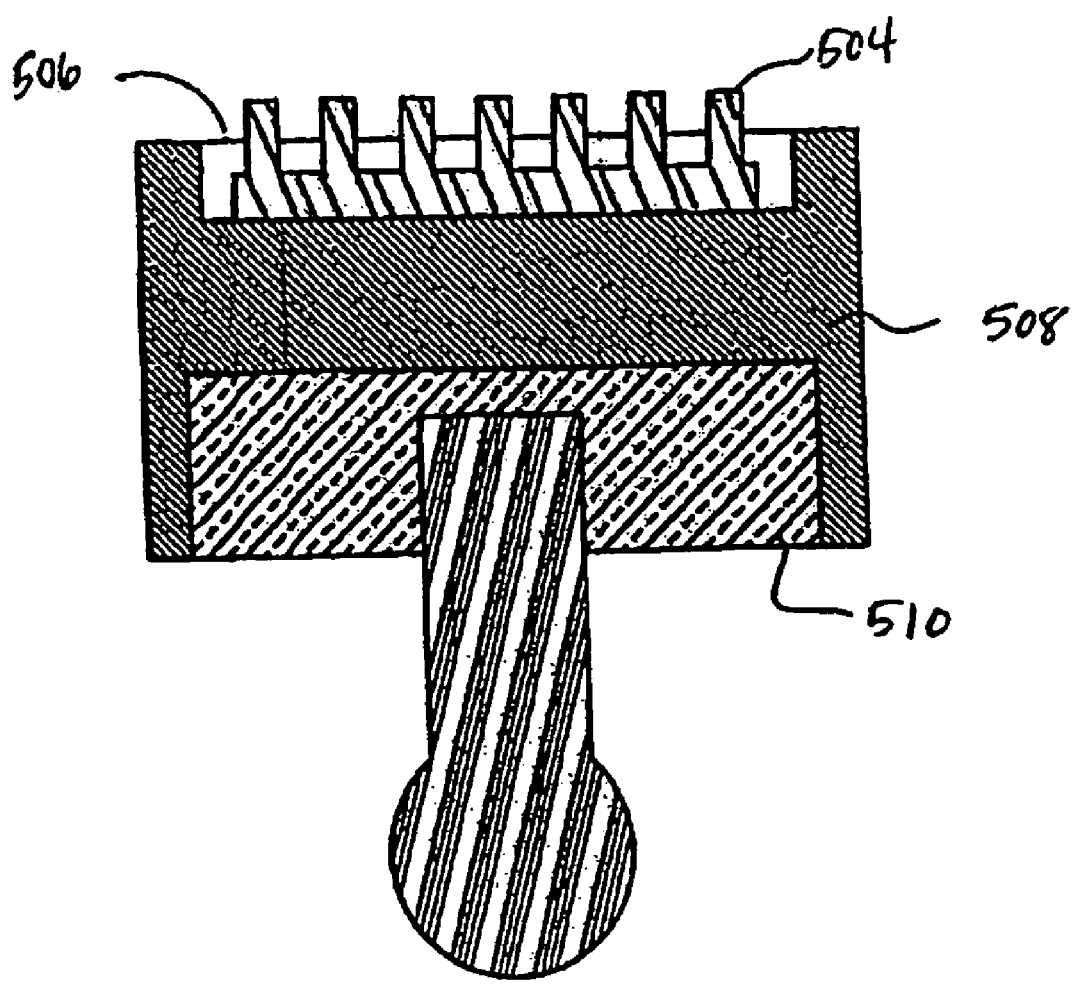
FIG. 9A is a cross-sectional view of the insert shown in FIG. 5A taken at line 5-5 having the molded, hooked traction elements extending partially above the level surface of the insert according to one variation of the invention.
Figure 9B:
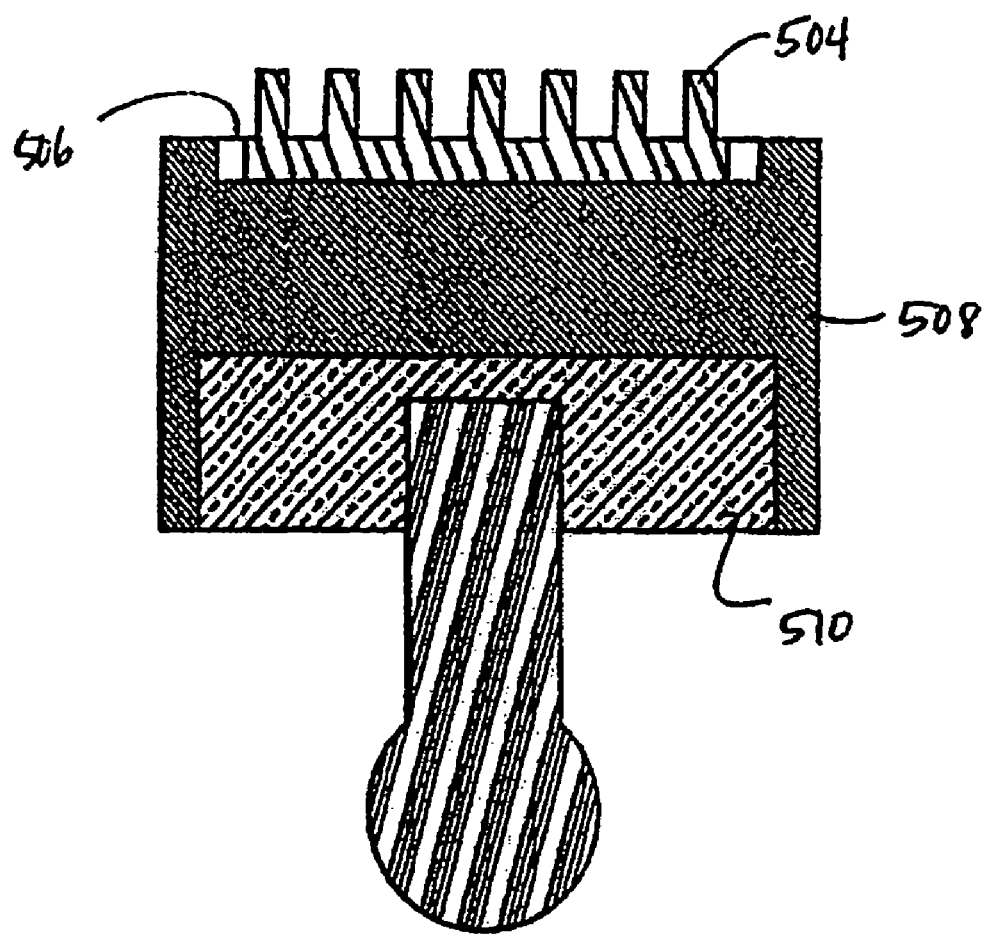
FIG. 9B is a cross-sectional view of an insert similar to that shown in FIG. 5A taken at line 5-5 having the molded, hooked traction elements extending further above the level surface of the insert.
Figure 9C:
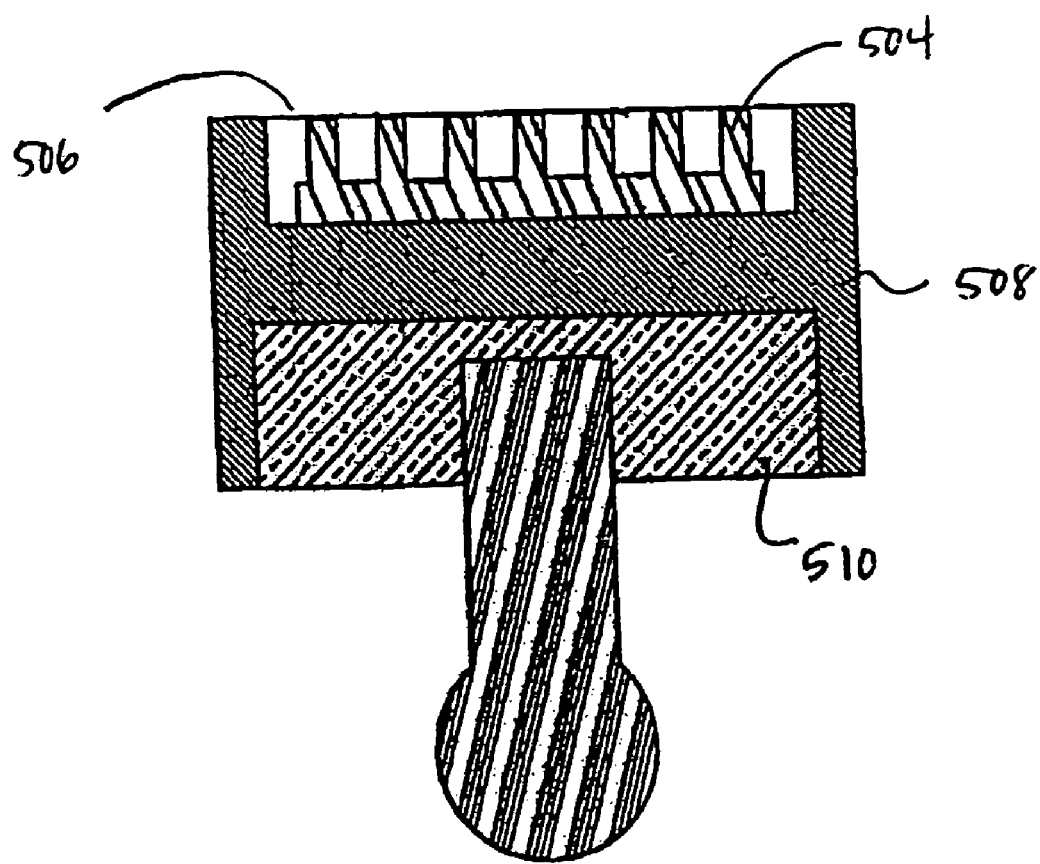
FIG. 9C is a cross-sectional view of the insert similar to that shown in FIG. 5A taken at line 5-5 with molded, hooked traction elements adapted to be level with the surface of the insert.
Figure 9D:
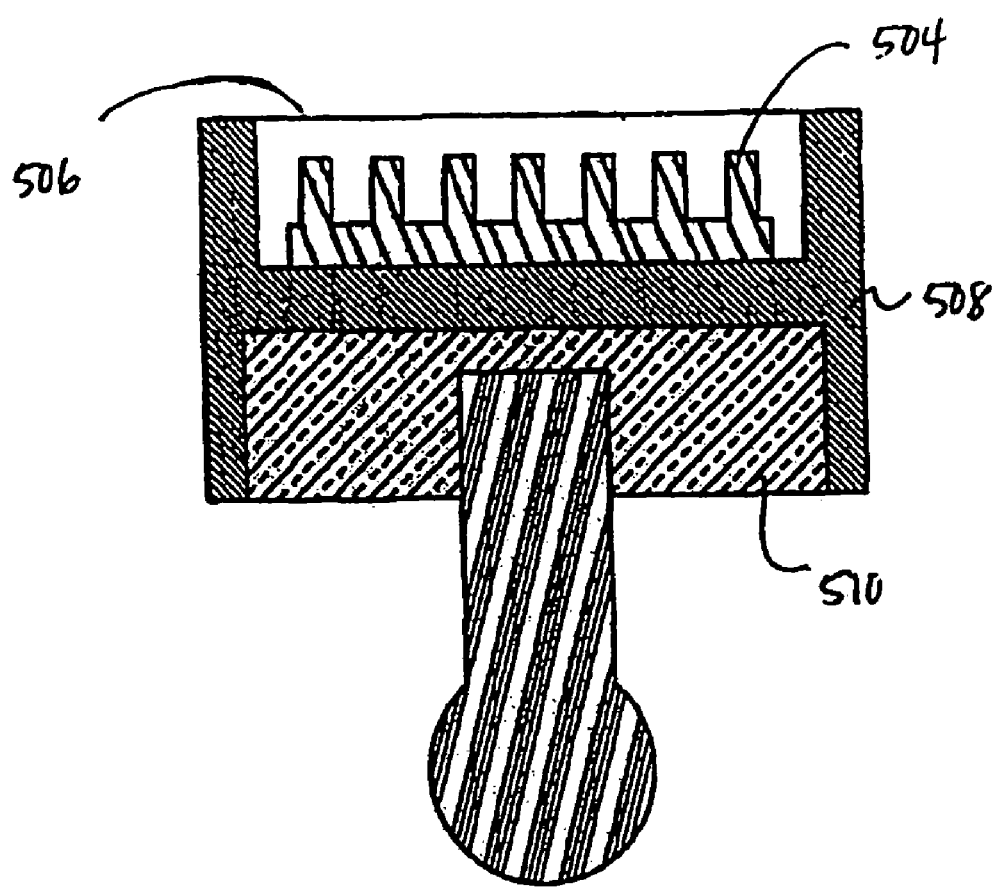
FIG. 9D is a cross-sectional view of the insert similar to that shown in FIG. 5A taken at line 5-5 with molded, hooked traction elements lying below the level surface of the insert.

The traction elements may also lie at varying positions relative to the level surface of the insert. For example, as mentioned, sheets, strips, or other patterned regions can be applied to insert contact surfaces, either into a flat contact surface of the insert, or into preformed, recessed regions of the insert that lie below the surface level of the insert. Examples of the latter scenario are depicted in FIGS. 9A-9D. A cross-sectional view of the insert taken at line 5-5 (FIG. 5A) shows traction elements 504 extending partially above the surface level of insert 506 (FIG. 9A). The traction elements 504 may also further extend from surface level 506 (FIG. 9B), or lie level with the surface level of insert 506 (FIG. 9C), or lie below level surface 506 (FIG. 9D).

The invention will be better understood by reference to the following examples, which are offered by way of illustration only and not by way of limitation.

EXAMPLES

Example 1

Tractive Force of Surgical Clamp Inserts

Surgical clamps containing jaw inserts according to the present invention were tested against known surgical clamps and jaw insert systems, and respective traction capabilities were measured. The surgical clamps clips were applied to porcine aortas that were pressurized to a blood pressure between 100 mmHg to 155 mmHg. The vessels were coated with whole milk at room temperature to lubricate the vessels, in order to simulate the condition of the vessels in the surgical field (in which blood vessels are typically covered on their outer surfaces by blood). Previous studies indicate that porcine vessels lubricated with whole milk closely match the physical properties of human cadaver vessels lubricated with actual blood. This system is thus a close approximation of actual surgical conditions.

The various inserts tested varied in their attachment mechanisms, and therefore different styles of surgical clamps that accommodated the various inserts were used accordingly. In each case, however, the clamping force applied to the vessel was between 5-6 lbf. More particularly, the applied force was measured with a force gauge and a fixture that kept the jaws maintained at a jaw spacing of 4 mm, which closely mimics conditions for clamping an aorta (average aorta wall thickness approximately 2 mm). Therefore the same clamping force was consistently applied across all the insert systems. To measure the tractive force imparted by each respective insert, each clamp was pulled radially (i.e., perpendicular to the axis of the vessel) off the clamped vessel a total of four times at a constant speed of 4 inches/minute, and the maximum tractive force exerted on the clamp to accomplish such radial movement during the process was recorded. The maximum force exerted was considered indicative of the tractive force applied by the inserts to the engaged vessel.

The following surgical clamps and surgical clamp insert systems were tested:

Insert Type 1. Inserts of foam overlaid with a woven layer of finger-like nylon projections available under tradename FIBRA™ Surgical Clamp Inserts (Applied Medical, Rancho Santa Margarita, Calif., Model No. G-8655). These inserts were attached to an Applied Medical 86 mm-0° surgical clamp (Applied Medical, Rancho Santa Margarita, Ca, Model No. A3312).

Insert Type 2. Inserts of a compliant, elastomeric pad molded onto a semi-rigid plastic base available under tradename INTRACK™ Double Traction Inserts (Novare Surgical, Cupertino, Calif., Model No. N-10146), secured to an INTRACK™ Clamp (Novare Surgical, Cupertino, Calif., Model No. N-10136). The inserts have a surface with repeating pyramid shapes.

Insert Type 3. Steel-jawed clamp without any insert, AES-CULAP™ clamp (Aescualp AG, Center Valley, Pa., Model No. FB532R-2007).

Figure 4B:
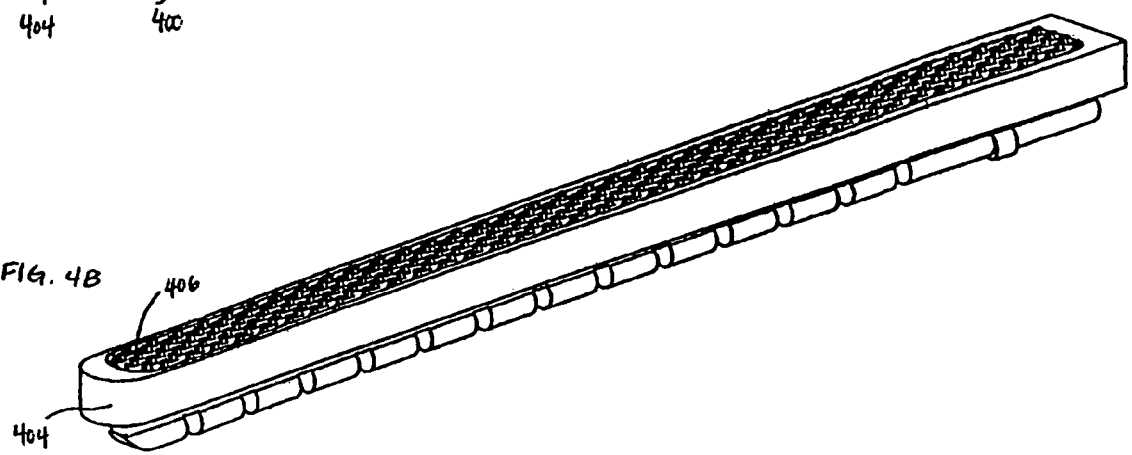
FIG. 4B is a perspective view of the insert shown in FIG. 4A.

Insert Type 4. Inserts formed of an elastomer and including molded, hooked traction elements according to the invention. The inserts include a continuous strip of uniform width of molded, hooked traction elements (Velcro 830/833, Velcro USA Inc., Manchester, N.H.) secured to the insert surface, as depicted in the embodiment of FIGS. 4A-4B. The molded, hooked traction elements have the general shape and orientation, and are generally arrayed, as shown FIGS. 2A-2C. The inserts were secured to an INTRACK™ Clamp (Novare Surgical, Cupertino, Calif., Model No. N-10136).

Insert Type 5. Inserts formed of an elastomer and including molded, hooked traction elements according to the invention. The inserts include a series of circle patterns of molded, hooked traction elements (ripngrip 2002 HM, ripngrip Industries Inc., Palmdale, Calif.) secured to the insert surface, as depicted in the embodiment of FIGS. 6A-6B. The molded, hooked traction elements have the general shape and orientation, and are generally arrayed, as shown FIGS. 1A-1C. The inserts were secured to an INTRACK™ Clamp (Novare Surgical, Cupertino, Calif., Model No. N-10136)

Insert Type 6. Inserts similar to those of Insert Type 5 formed of an elastomer and including molded, hooked traction elements according to the invention. The inserts include a series of circle patterns of molded, hooked traction elements (ripngrip 2002 HM, ripngrip Industries Inc., Palmdale, Calif.) secured to the insert surface, as depicted in the embodiment of FIGS. 6C-6D (the circles are spaced further apart than those of Insert Type 5). The molded, hooked traction elements have the general shape and orientation, and are generally arrayed, as shown FIGS. 1A-1C. The inserts were secured to an INTRACK™ Clamp (Novare Surgical, Cupertino, Calif., Model No. N-10136).

Insert Type 7. Inserts formed of an elastomer and including molded, hooked traction elements according to the invention. The inserts include a series of oval patterns of molded, hooked traction elements (Velcro 830/833, Velcro USA Inc., Manchester, N.H.) secured to the insert surface, as depicted in the embodiment of FIGS. 7A-7B. The molded, hooked traction elements have the general shape and orientation, and are generally arrayed, as shown FIGS. 2A-2C. The inserts were secured to an INTRACK™ Clamp (Novare Surgical, Cupertino, Calif., Model No. N-10136).

Insert Type 8. Inserts formed of an elastomer and including molded, hooked traction elements according to the invention. The inserts include a continuous strip of with alternating segments of narrow and corresponding wider widths of molded, hooked traction elements (ripngrip 2002 HM, ripngrip Industries Inc., Palmdale, Calif.) secured to the insert surface, as depicted in the embodiment of FIGS. 5A-5B. The molded, hooked traction elements have the general shape and orientation, and are generally arrayed, as shown FIGS. 1A-1C. The inserts were secured to an INTRACK™ Clamp (Novare Surgical, Cupertino, Calif., Model No. N-10136).

Insert Type 9. Inserts formed of an elastomer and including molded, hooked traction elements according to the invention. The inserts include a series of diamond-shaped patterns of molded, hooked traction elements (Velcro 830/833, Velcro USA Inc., Manchester, N.H.) secured to the insert surface, as depicted in the embodiment of FIGS. 8A-8B. The molded, hooked traction elements have the general shape and orientation, and are generally arrayed, as shown FIGS. 2A-2C. The inserts were secured to an INTRACK™ Clamp (Novare Surgical, Cupertino, Calif., Model No. N-10136).

Insert Type 10. Inserts formed of an elastomer and including molded, hooked traction elements according to the invention. The inserts include a continuous strip, hooked traction elements (obtained from fastener materials on disposable absorbent articles sold under the brand name Ultra Comfort™, Kroger Co., Cincinnati, Ohio) secured to the insert surface. The molded, hooked traction elements have the general shape and orientation, and are generally arrayed, as shown FIGS. 3A-3C. The inserts were secured to an INTRACK™ Clamp (Novare Surgical, Cupertino, Calif., Model No. N-10136).

The results of the radial pull tests are indicated in Table I below, including individual recorded pull off forces, and average pull-off force, for each insert type.

TABLE I

| Insert Type | Average Pull-Off Force (lbf) | Trial 1 (lbf) | Trial 2 (lbf) | Trial 3 (lbf) | Trial 4 (lbf) |
| --- | --- | --- | --- | --- | --- |
| 1 | 2.4 | 2.3 | 3.1 | 2.4 | 2.0 |
| 2 | 2.4 | 2.5 | 2.3 | 2.4 | 2.4 |
| 3 | ≧7.7 | 5.7 | 10+* | 6.4 | 8.6 |
| 4 | 7.7 | 8.6 | 6.8 | 8.0 | 7.3 |

TABLE I-continued

| Insert Type | Average Pull-Off Force (lbf) | Trial 1 (lbf) | Trial 2 (lbf) | Trial 3 (lbf) | Trial 4 (lbf) |
|---|---|---|---|---|---|
| 5 | ≧8.1 | 10+* | 10+* | 7.1 | 5.4 |
| 6 | 5.4 | 7.0 | 5.2 | 5.3 | 4.0 |
| 7 | ≧6.8 | 10+* | 6.9 | 5.4 | 4.9 |
| 8 | ≧7.1 | 10+* | 7.6 | 5.8 | 5.2 |
| 9 | ≧8.2 | 10+* | 10+* | 7.4 | 5.3 |
| 10 | ≧7.6 | 10+* | 7.8 | 7.3 | 5.2 |

*Maximum load on the measuring force gauge was 10 lbf, and a result of 10+ indicates that the test was stopped when 10 lbf was reached. Therefore, for inserts giving a trial result of 10+, the average pull-off force could be higher than that calculated.

The results of the clamp pull-off tests indicate that the inserts according to embodiments of the present invention, i.e., Insert Types 4-10, provide more traction than known Insert Types 1 and 2, specifically, over 2-3 times more tractive force, depending on the insert. Furthermore, many of these inserts provided for a tractive force that met or exceeded that supplied by a conventional steel jawed clamp (average 7.7 lbf). It was previously unexpected that atraumatic inserts could achieve the degree of traction found with conventional steel jaw clamps.

Example 2

Tractive Force of Surgical Clips

Surgical clips containing jaw inserts according to the present invention were tested against known surgical clips, and respective traction capabilities were measured, according to the methods described above in Example 1. The surgical clips tested were of the parallel-jaw, spring clip variety. The clamping force exerted by each tested clip ranged from 0.85-1.00 lbs. (full force). Again, the attached clips were radially pulled off the vessel at a constant speed and the maximum force exerted on the clamp during the process was recorded. The maximum force exerted is considered indicative of the tractive force applied by the inserts to the engaged vessel.

The following surgical clips and clip insert systems were tested:

Insert Type A. Soft jaw inserts of foam overlaid with a woven layer of finger-like nylon projections (FIBRA™ Surgical Clip, Applied Medical, Rancho Santa Margarita, Calif., Model No. G-6050).

Insert Type B. Elastomeric soft jaw inserts having integrally formed repeating ridges extending across the width of the insert surface, with the ridges being approximately 0.007 inches high and 0.010 inches wide, as further described in U.S. application Ser. No. 10/349,871, filed Jan. 22, 2003, and incorporated herein in its entirety. (Greyhound, Novare Surgical, Cupertino, Calif., Model No. N-10157)

Insert Type C. Inserts formed of an elastomer and including molded, hooked traction elements according to the invention. The inserts include a continuous strip of uniform width of molded, hooked traction elements (Velcro 830/833, Velcro USA Inc., Manchester, N.H.) secured to the insert surface. The molded, hooked traction elements have the general shape and orientation, and are generally arrayed, as shown FIGS. 2A-2C. The inserts were secured to a Greyhound style surgical clip, in substitution of the conventional insert surface (Greyhound, Novare Surgical, Cupertino, Calif., Model No. N-10157)

Insert Type D. Soft jaw inserts of natural sponge rubber with smooth surface, and an interior cavity running the length of the insert (Fogarty Softjaw™ Spring Clip, Edwards Life Sciences, Irvine, Calif., Model No. CSOFT6)

The results of the radial pull tests are indicated in Table II below, including individual recorded pull off forces, and average pull-off force, for each insert type.

TABLE II

| Insert Type | Average Pull-Off Force (lbf) | Trial 1 (lbf) | Trial 2 (lbf) | Trial 3 (lbf) | Trial 4 (lbf) |
|---|---|---|---|---|---|
| A | 0.2 | 0.2 | 0.2 | 0.2 | 0.2 |
| B | 0.6 | 0.5 | 0.6 | 0.5 | 0.6 |
| C | 1.8 | 1.4 | 1.7 | 1.7 | 2.2 |
| D | 0.4 | 0.4 | 0.3 | 0.4 | 0.4 |

The results of the clip pull-off tests indicate that the surgical clips with Type C inserts provide 9 times more traction than Type A inserts, 3 times more traction than Type B inserts, and approximately 4.5 times more traction than Type D inserts.

* * *

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed as new and desired to be protected by Letters Patent of the United States is:

1. An insert for attachment to a surgical instrument adapted for contacting tissue, said insert comprising a compliant cushion having a tissue-engaging contact surface and having a plurality of molded, hooked traction elements on at least a region of said surface, wherein said hooked traction elements are integrally formed with said tissue engaging contact surface, and wherein said hooked traction elements are not more than 1 mm in height.

2. The insert of claim 1 wherein said molded, hooked traction elements are configured to have at least one crook.

3. The insert of claim 1 wherein said molded, hooked traction elements are configured to have at least two crooks.

4. The insert of claim 1 wherein said molded, hooked traction elements are configured to have a mushroom-like shape.

5. The insert of claim 1 wherein said molded, hooked traction elements are not more than about 0.5 mm in height.

6. The insert of claim 1 wherein said molded, hooked traction elements are not more than about 0.3 mm in height.

7. The insert of claim 1 wherein the density of said molded, hooked traction elements on said surface region is at least about 100/cm².

8. The insert of claim 1 wherein the density of said molded, hooked traction elements on said surface region is at least about 130/cm².

9. The insert of claim 1 wherein the density of said molded, hooked traction elements on said surface region is at least about 260/cm².

10. The insert of claim 1 wherein the density of said molded, hooked traction elements on said surface region is at least about 300/cm$^2$.

11. An insert for attachment to a surgical instrument adapted for contacting tissue, said insert comprising a compliant cushion having a tissue-engaging contact surface and having a plurality of hooked traction elements on at least a region of said surface at a density on said surface region of at least about 100/cm$^2$, wherein said hooked traction elements are integrally formed with said tissue engaging contact surface, and wherein said hooked traction elements are not more than 1 mm in height.

12. The insert of claim 11 wherein the density of said hooked traction elements on said surface region is at least about 130/cm$^2$.

13. The insert of claim 11 wherein the density of said hooked traction elements on said surface region is at least about 260/cm$^2$.

14. The insert of claim 11 wherein the density of said hooked traction elements on said surface region is at least about 300/cm$^2$.

15. A surgical instrument comprising a compliant tissue engaging surface, the surface having a plurality of hooked traction elements on at least a region of said surface at a density on said surface region of at least about 100/cm$^2$, wherein said hooked traction elements are integrally formed with said tissue engaging contact surface, and wherein said hooked traction elements are not more than 1 mm in height.

16. The surgical instrument of claim 15 wherein the density of said hooked traction elements on said surface region is at least about 130/cm$^2$.

17. The surgical instrument of claim 15 wherein the density of said hooked traction elements on said surface region is at least about 260/cm$^2$.

18. The surgical instrument of claim 15 wherein the density of said hooked traction elements on said surface region is at least about 300/cm$^2$.

19. An insert for attachment to a surgical instrument adapted for contacting tissue, said insert comprising a compliant cushion having a tissue-engaging contact surface and having a plurality of hooked traction elements on at least a region of said surface, wherein said traction elements are not more than 1 mm in height, and wherein said hooked traction elements are integrally formed with said tissue engaging contact surface.

20. The insert of claim 19 wherein said hooked traction elements are not more than about 0.5 mm in height.

21. The insert of claim 19 wherein said hooked traction elements are not more than about 0.3 mm in height.

22. A surgical instrument comprising a compliant tissue engaging surface, the surface having a plurality of hooked traction elements on at least a region of said surface, wherein said hooked traction elements are integrally formed with said tissue engaging contact surface, and wherein said hooked traction elements are not more than 1 mm in height.

23. The surgical instrument of claim 22 wherein said hooked traction elements are not more than about 0.5 mm in height.

24. The surgical instrument of claim 22 wherein said hooked traction elements are not more than about 0.3 mm in height.

25. A method of retracting selected tissue comprising the steps of: (a) providing a surgical instrument having a compliant tissue engaging surface adapted for retracting tissue, the surface having a plurality of molded, hooked traction elements on at least a region of said surface, wherein said hooked traction elements are integrally formed with said tissue engaging contact surface, and wherein said hooked traction elements are not more than 1 mm in height; (b) contacting said surface with the selected tissue; and (c) actuating said instrument such that said selected tissue is retracted.

26. A method of stabilizing or immobilizing selected tissue or organ comprising the steps of:
(a) providing a surgical instrument having a compliant tissue engaging surface adapted for stabilizing or immobilizing the selected tissue or organ, the surface having a plurality of molded, hooked traction elements on at least a region of said surface, wherein said hooked traction elements are integrally formed with said tissue engaging contact surface, and wherein said hooked traction elements are not more than 1 mm in height;
(b) contacting said surface with the selected tissue or organ;
and (c) actuating said instrument to stabilize or immobilize said tissue or organ.

27. A method of grasping selected tissue or organ comprising the steps of: (a) providing a surgical instrument having a compliant tissue engaging surface adapted for grasping the selected tissue or organ, the surface having a plurality of molded, hooked traction elements on at least a region of said surface, wherein said hooked traction elements are integrally formed with said tissue engaging contact surface, and wherein said hooked traction elements are not more than 1 mm in height; (b) contacting said surface with the selected tissue or organ; and (c) actuating said instrument to grasp said tissue or organ.

\* \* \* \* \*